US00PP35039P2

(12) United States Plant Patent
Valstar

(10) Patent No.: US PP35,039 P2
(45) Date of Patent: Mar. 14, 2023

(54) ***CTENANTHE* PLANT NAMED 'VALCOSTA2'**

(50) Latin Name: *Ctenanthe oppenheimiana*
Varietal Denomination: VALCOSTA2

(71) Applicant: Gebr. Valstar Beheer B.V., Maasland (NL)

(72) Inventor: Oscar Valstar, Maasland (NL)

(73) Assignee: Gebr. Valstar Beheer B.V., Maasland (NL)

( * ) Notice: Subject to any disclaimer, the term of this patent is extended or adjusted under 35 U.S.C. 154(b) by 0 days.

(21) Appl. No.: 17/803,416

(22) Filed: Jun. 27, 2022

(51) Int. Cl.
*A01H 5/12* (2018.01)
*A01H 6/00* (2018.01)

(52) U.S. Cl.
USPC ..... Plt./263.1
CPC ..... *A01H 6/00* (2018.05)

(58) Field of Classification Search
USPC ..... Plt./263.1, 373
CPC ..... A01H 6/00
See application file for complete search history.

(56) References Cited

PUBLICATIONS

Plant Breeder's Rights to a *Ctenanthe* plant named, 'VALCOSTA2', QZ PBR 2021/2548, filed Oct. 11, 2021.*

* cited by examiner

*Primary Examiner* — Anne Marie Grunberg
(74) *Attorney, Agent, or Firm* — Samuel R. McCoy, Jr.

(57) ABSTRACT

'VALCOSTA2' is a new and distinctive *Ctenanthe* plant which is characterized by foliage with large laminae borne on long, upright petioles that arise directly from the base of the plant, a light greyed-green adaxial laminar surface with broad portions of the lamina adjacent to veins prominently colored with a mixture of dark green to yellow-green, an abaxial laminar surface which is colored with a mixture of dark greyed-purple and brown and lightly suffused with yellow-green at the margins, and the stability of all characteristics from generation to generation. The new variety is typically produced as an indoor ornamental plant.

3 Drawing Sheets

Latin name of the genus and species: The Latin name of the genus and species of the novel variety disclosed herein is *Ctenanthe oppenheimiana.*

Variety denomination: The inventive variety of *Ctenanthe* disclosed herein has been given the variety denomination 'VALCOSTA2'.

CROSS REFERENCE TO RELATED APPLICATIONS

This application claims priority to the Community Plant Variety Rights application number 2021/2548, filed Oct. 11, 2021, which is herein incorporated by reference.

BACKGROUND OF THE INVENTION

Parentage: The claimed plant originated as a naturally occurring, whole-plant mutation. In May of 2017, the inventor discovered a plurality of whole-plant mutations at his commercial greenhouse in Maasland, the Netherlands, growing amongst a cultivated population of *Ctenanthe oppenheimiana* 'Compactstar' (not patented) plants. The newly discovered plants were isolated for further observation in order to confirm the distinctness and stability of the characteristics first observed. After further evaluation it was determined that one plant, in particular, exhibited unique foliage coloration and a growth habit that would prove favorable for commercial marketability. The new variety was given the denomination 'VALCOSTA2'.

Asexual Reproduction: Asexual reproduction of 'VALCOSTA2', by way of leaf cuttings, was first performed in May of 2017 at the inventor's commercial greenhouse in Maasland, the Netherlands. 'VALCOSTA2' was subsequently reproduced by way of meristematic tissue culture as well. Eighteen successive generations so produced have shown that the unique features of the instant cultivar are stable and reproduced true to type.

SUMMARY OF THE INVENTION

The cultivar 'VALCOSTA2' has not been observed under all possible environmental conditions and the phenotype may vary somewhat with variations in the instant environment such as temperature, day length, and light intensity, without, however, any variance in genotype. The following characteristics have been repeatedly observed and represent the distinguishing characteristics of the new *Ctenanthe* cultivar 'VALCOSTA2'. These traits, in combination, distinguish 'VALCOSTA2' as a new and distinct cultivar.

1. *Ctenanthe* 'VALCOSTA2' exhibits foliage with large laminae borne on long, upright petioles that arise directly from the base of the plant; and
2. *Ctenanthe* 'VALCOSTA2' exhibits greyed-green to yellow-green petioles that are strongly suffused with greyed-purple on the abaxial surface; and
3. *Ctenanthe* 'VALCOSTA2' exhibits an adaxial laminar surface which is colored light greyed-green, with broad portions of the lamina adjacent to veins prominently colored with a mixture of green to yellow-green, creating a unique color pattern; and 4. *Ctenanthe* 'VALCOSTA2' exhibits an abaxial laminar surface which is colored with a mixture of dark greyed-purple and brown and lightly suffused with yellow-green at the margins.

BRIEF DESCRIPTION OF THE FIGURES

The photographs were taken using conventional techniques and although colors may appear different from actual colors due to light reflectance it is as accurate as possible by conventional photographic techniques.

BOTANICAL DESCRIPTION OF THE PLANT

Figure 1:
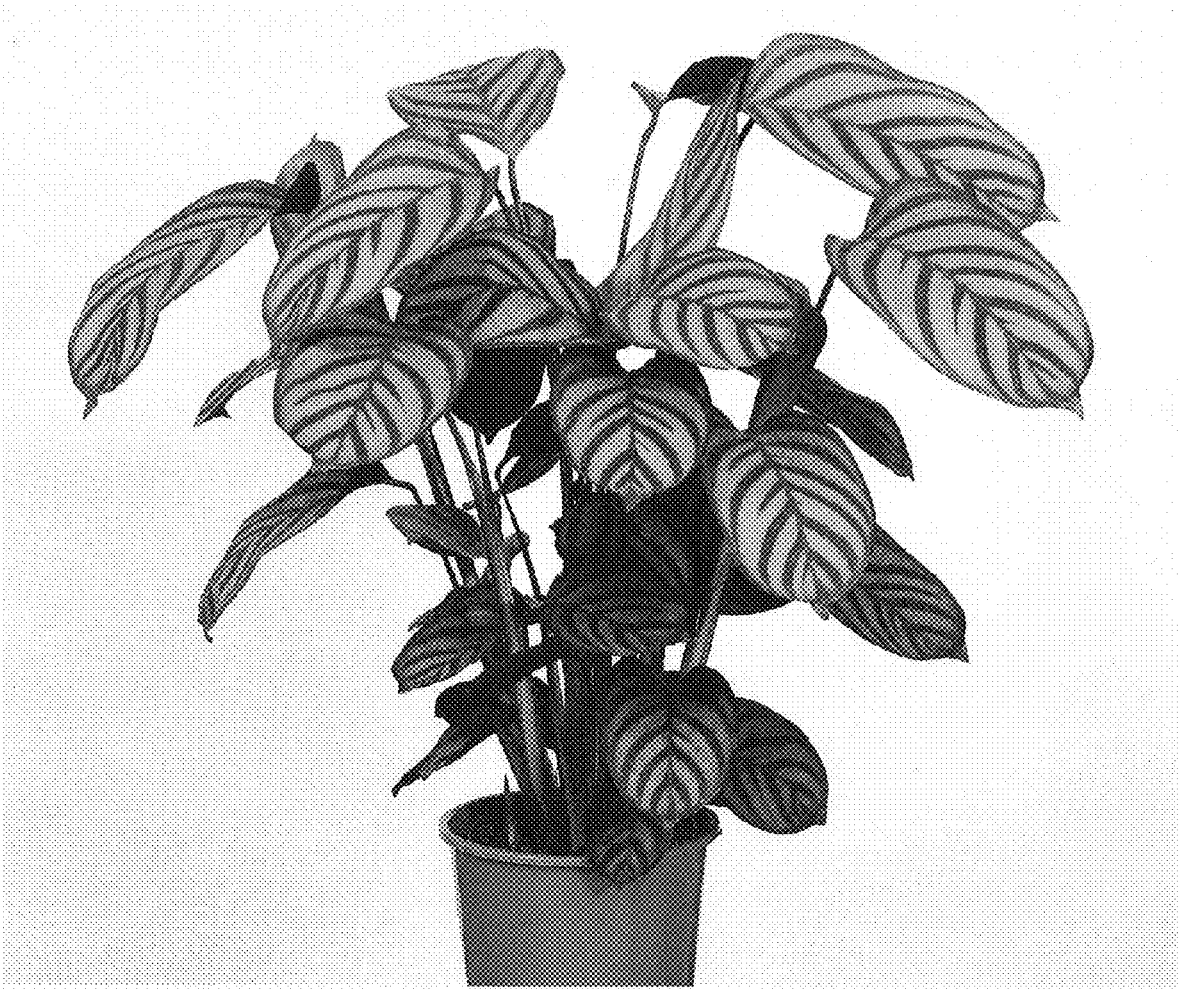
FIG. 1 shows, as nearly true as it is reasonably possible to make the same in color illustrations of this type, an exemplary plant of the new cultivar, 'VALCOSTA2'. The plant shown is approximately 12 months old from a rooted cutting, potted into a 17 cm nursery container, grown in a climate-controlled greenhouse in Maasland, the Netherlands.
Figure 2:
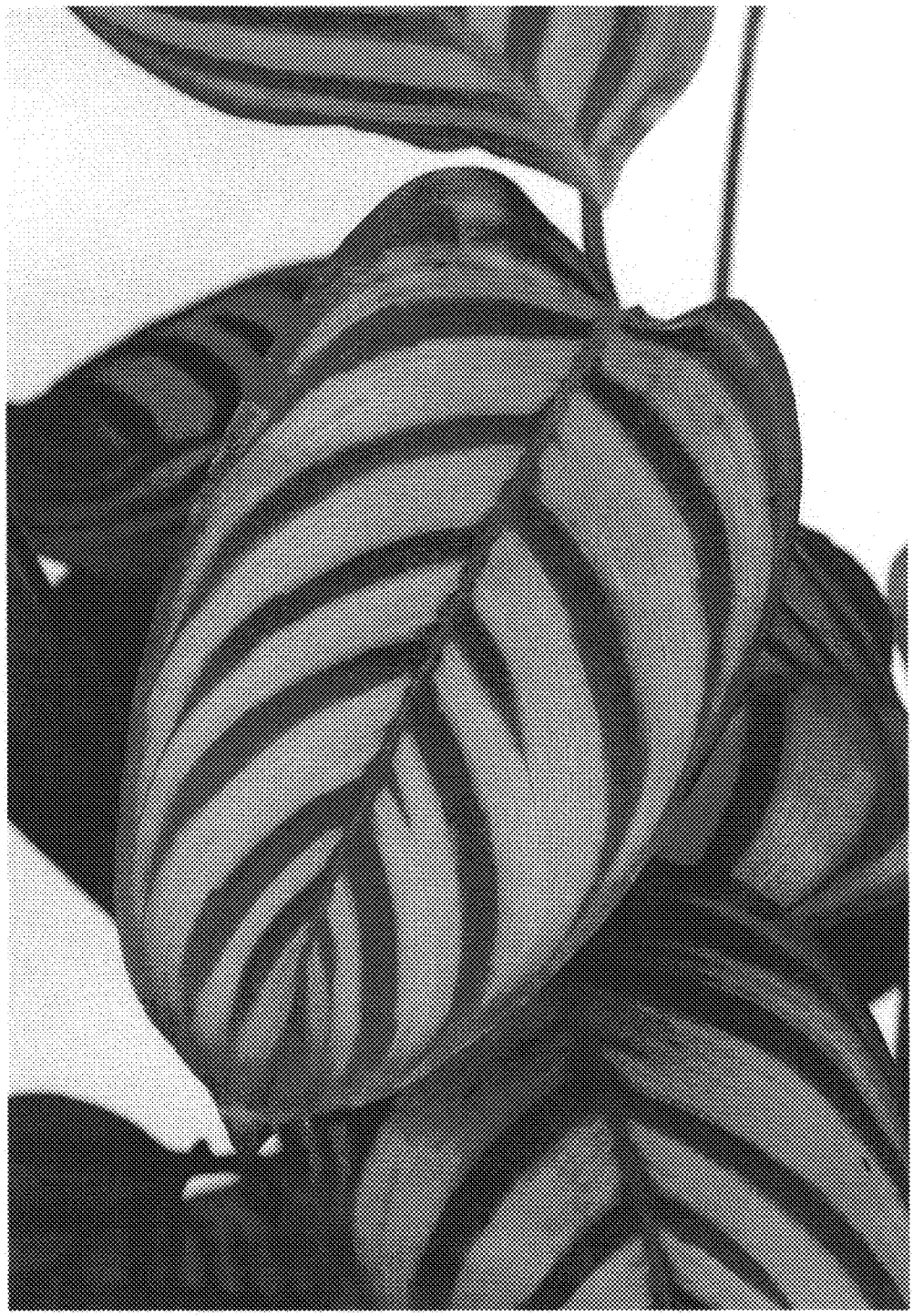
FIG. 2 shows, as nearly true as it is reasonably possible to make the same in color illustrations of this type, the adaxial surface of the mature foliage of the claimed plant.
Figure 3:
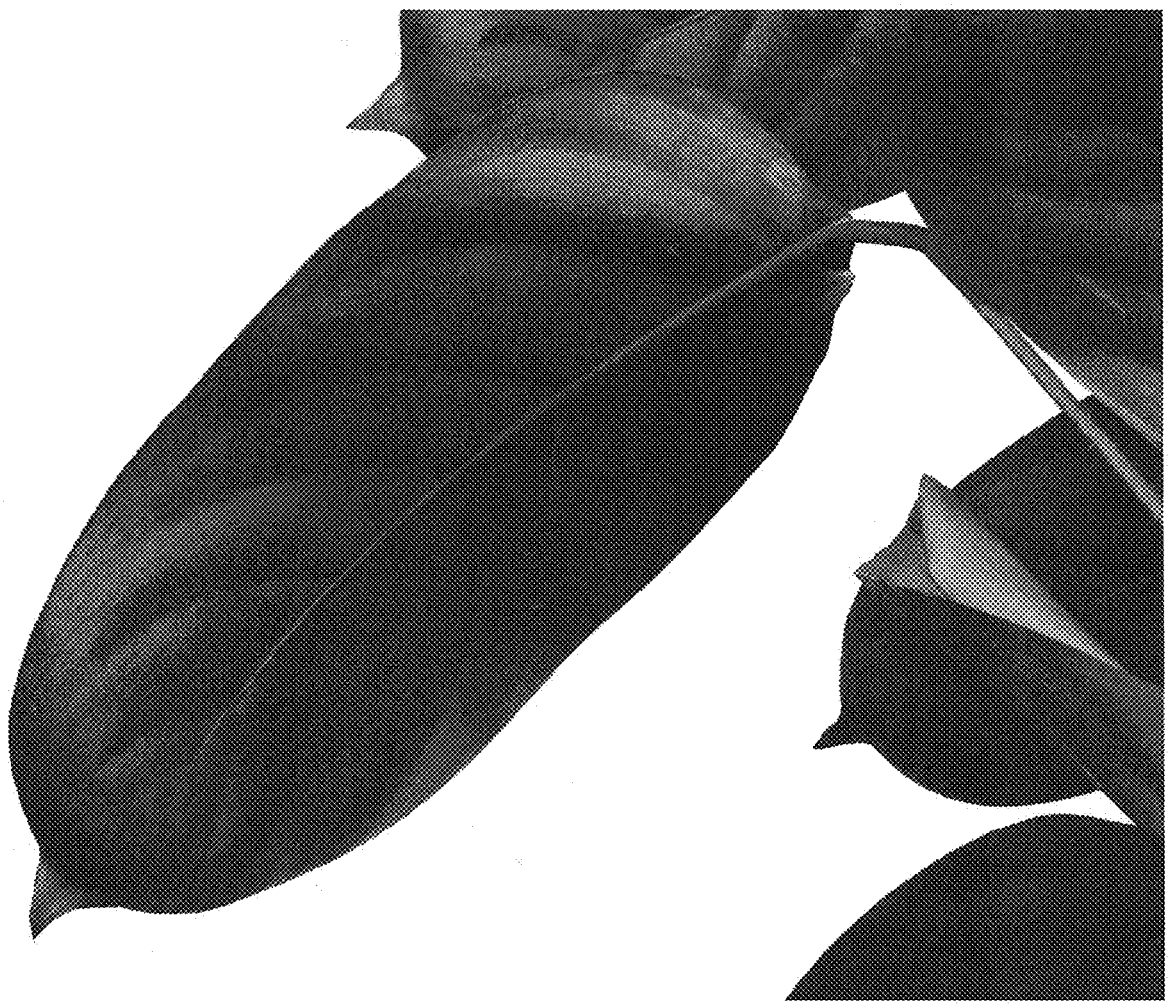
FIG. 3 shows, as nearly true as it is reasonably possible to make the same in color illustrations of this type, the abaxial surface of the mature foliage of the claimed plant.

The following observations and measurements made in October of 2021 describe averages from a sample set of six specimens of 1 year old 'VALCOSTA2' plants grown in 17 cm nursery containers at commercial greenhouse in Maasland, the Netherlands. Plants were produced using conventional greenhouse production protocols for *Ctenanthe* which consisted of growing under shade cloth, regular overhead irrigation, and fertilizer applications as needed. No chemical pest and disease control measures were taken. No photoperiodic treatments or artificial light was given to the plants.

Those skilled in the art will appreciate that certain characteristics will vary with older or, conversely, with younger plants. 'VALCOSTA2' has not been observed under all possible environmental conditions. Where dimensions, sizes, colors and other characteristics are given, it is to be understood that such measurements are approximations or averages set forth as accurately as practicable. The phenotype of the variety may differ from the descriptions set forth herein with variations in environmental, climactic and cultural conditions. Color notations are based on *The Royal Horticultural Society Colour Chart*, The Royal Horticultural Society, London, Sixth Edition.

A botanical description of 'VALCOSTA2' and comparisons with the parent and the most similar variety of common knowledge are provided below.

General plant description:

*Growth habit*.—Clump forming; upright with foliage arising directly from the base of each clump.

*Plant profile*.—Broad obovate with flattened top.

*Height*.—47.3 cm in height, to the highest leaf.

*Width*.—Average 61.2 cm in width.

*Growth rate*.—Moderately fast growing.

*Plant vigor*.—Moderately to highly vigorous.

*Propagation*.—Method — Meristematic tissue culture. Time to initiate roots — Approximately 8 weeks to initiate roots at approximately 20 degrees Centigrade. Crop time — Approximately 20 weeks to produce a well-rooted 10 cm container from a rooted cutting.

*Environmental tolerances*.—Moderately high tolerance to rain; low to moderate tolerance to wind; tolerant of temperatures to at least 40 degrees Celsius. Cold hardy to USDA Hardiness Zone 10.

*Pest resistance and susceptibility*.—Plants have not been observed to be any more or less susceptible or resistant to pathogens and pests common to *Ctenanthe* sp.

Root system:

*Branching*.—Moderately branched.

*Density*.—Moderately dense.

*Distribution*.—Roots are moderately deep.

*Diameter*.—0.2 cm.

*Texture*.—Fleshy; smooth; lacking root hairs.

*Color*.—Greyed-yellow, nearest to RHS 161C.

Stems:

*Branching characteristics*.—Clumping plant with leaves emerging directly from the base of the plant; no main stems or lateral branching.

Foliage:

*Arrangement*.—Alternate; equitant.

*Division*.—Simple.

*Attachment*.—Petiolate.

*Quantity of leaves per shoot*.—Average of 4.

*Quantity of shoots per plant*.—Average of 7.

*Quantity of leaves per plant*.—Approximately 28.

*Lamina*.—Shape — Oblong. Apex — Abruptly acute. Base — Acute to short attenuate. Aspect — Flat to very slightly carinate. Attitude — Upright and outward. Dimensions — 19.9 cm long and 9.8 cm wide. Margin — Entire; very slight coarse undulation. Texture and luster, adaxial surface — Smooth, glabrous, and matte. Texture and luster, abaxial surface — Smooth, glabrous, and matte. Juvenile color, adaxial surface — Yellow-green, nearest to a mixture of RHS 145C, 145D, and 147D. A portion of the lamina adjacent to veins is colored with a darker shade of yellow-green, nearest to a mixture of RHS 144A and N144C. Juvenile color, abaxial surface — Yellow-green, nearest to RHS 145A, and lightly to very strongly suffused with greyed-brown, nearest to RHS N199B. Mature color, adaxial surface — Greyed-green, nearest to a mixture of RHS 189A and 191A. A broad portion of the lamina adjacent to veins is prominently colored with a mixture of green to yellow-green, RHS 139A and 147A. Mature color, abaxial surface — Nearest to a mixture of greyed-purple and brown, RHS N186C and 200B, and lightly suffused with yellow-green at the margins, nearest to RHS 147A. Venation — Vein pattern — Pinnate. Vein color, adaxial surface — Green, nearest to in between RHS NN137B and NN137C. Vein color, abaxial surface — Greyed-purple, nearest to RHS 183A.

*Petiole, excluding geniculum*.—Length — Approximately 40.0 cm. Width — Approximately 0.5 cm at the proximal end and 0.3 cm at the distal end. Strength — Strong. Texture — Smooth; sparsely to moderately covered with short hairs with an average length of 0.1 cm; colored greyed-white, nearest to in between RHS 156C and 156D. Luster — Slightly glossy. Color, adaxial surface — Greyed-green, nearest to RHS 197A, and fading to yellow-green towards the proximal end, nearest to RHS 148D. Color, abaxial surface — Greyed-green, nearest to RHS 197A, and fading to yellow-green towards the proximal end, nearest to RHS 148D. Petiole is strongly suffused with greyed-purple, nearest to RHS 183A. Geniculum — Length — Approximately 1.9 cm. Width — Approximately 0.4 cm. Texture and Luster — Smooth, glabrous and matte. Color — Nearest to a mixture of yellow-green and brown, RHS 148A and N200A. Sheath — Length — 21.3 cm. Width — Approximately 0.4 cm. Margins — Ciliate; short, soft hairs with an average length of 0.2 cm and colored greyed-white, nearest to a mixture of RHS 156A, 156B, 156C, and 156D. Color, adaxial surface — Yellow-green, nearest to RHS 145D, and narrowly margined with greyed-purple, nearest to RHS 183A. Color, abaxial surface — Yellow-green, nearest to RHS 145D, and narrowly margined with greyed-purple, nearest to RHS 183A.

Inflorescence: No flowering has been observed, to date.

Flower buds: No flowering has been observed, to date.

Flowers: No flowering has been observed, to date.

Reproductive organs: No flowering has been observed, to date.

Seed and fruit: Seed production has not been observed.

Comparisons With the Parent

Plants of the new cultivar 'VALCOSTA2' may be distinguished from the parent, *Ctenanthe oppenheimiana* 'Compactstar' (unpatented), by the characteristics described in Table 1.

TABLE 1

| Characteristic | 'VALCOSTA2' | 'Compactstar' |
|---|---|---|
| Abundance of foliage. | Fewer than 'Compactstar'. | More than 'VALCOSTA2'. |
| Foliage size. | Larger than 'Compactstar'. | Smaller than 'VALCOSTA2'. |
| Petiole thickness. | Thicker than 'Compactstar'. | Thinner than 'VALCOSTA2'. |
| Foliar margin undulation. | Slight coarse undulation. | Typically, without undulation; occasionally slightly undulated. |
| General coloration of the mature foliage. | Foliage coloration and pattern is similar in both cultivars. However, the greyed-green portions of the lamina are lighter and the yellow-green portions are darker, making the color pattern more prominent. | Foliage coloration and pattern is similar in both cultivars. However, the greyed-green portions of the lamina are darker and the yellow-green portions are lighter, making the color pattern less prominent. |

Comparisons With the Most Similar Variety of Common Knowledge

Plants of the new cultivar 'VALCOSTA2' may be distinguished from the commercial variety *Ctenanthe* 'Silverstar' (not patented) by the characteristics described in Table 1.

TABLE 1

| Characteristic | 'VALCOSTA2' | 'Silverstar' |
|---|---|---|
| General coloration of the mature foliage. | Foliage coloration and pattern is similar in both cultivars. However, the yellow-green portions are both broader and darker, making the color pattern more prominent. | Foliage coloration and pattern is similar in both cultivars. However, the yellow-green portions are lighter and narrower, making the color pattern less prominent. |

That which is claimed is:

1. A new and distinct variety of *Ctenanthe* plant named 'VALCOSTA2', substantially as described and illustrated herein.

* * * * *